United States Patent
Ketkar et al.

(10) Patent No.: US 6,639,214 B1
(45) Date of Patent: Oct. 28, 2003

(54) METHOD OF IMPROVING THE PERFORMANCE OF AN ION MOBILITY SPECTROMETER USED TO DETECT TRACE ATMOSPHERIC IMPURITIES IN GASES

(75) Inventors: Suhas Narayan Ketkar, Allentown, PA (US); Seksan Dheandhanoo, Quakertown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/567,387

(22) Filed: May 9, 2000

(51) Int. Cl.[7] ............................................. B01D 59/44
(52) U.S. Cl. .................. 250/287; 250/282; 250/288; 250/424; 250/283; 250/41.9; 422/98; 73/23
(58) Field of Search .................. 250/287, 282, 250/288, 424, 283, 41.9; 422/98; 73/23

(56) References Cited

U.S. PATENT DOCUMENTS

| | | | |
|---|---|---|---|
| 3,621,239 A | 11/1971 | Cohen | 250/41.9 |
| 4,238,678 A | 12/1980 | Castleman et al. | 250/381 |
| 4,551,624 A * | 11/1985 | Spangler et al. | 250/282 |
| 5,032,721 A | 7/1991 | Bacon et al. | 250/282 |
| 5,095,206 A | 3/1992 | Bacon, Jr. et al. | 250/282 |
| 5,283,199 A | 2/1994 | Bacon, Jr. et al. | 436/173 |
| 5,405,781 A * | 4/1995 | Davies et al. | 250/282 |
| 5,457,316 A | 10/1995 | Cohen et al. | 250/286 |
| 5,968,837 A | 10/1999 | Doring et al. | 436/173 |
| 6,144,029 A * | 11/2000 | Adler | 250/286 |
| 6,323,482 B1 * | 11/2001 | Clemmer et al. | 250/287 |

OTHER PUBLICATIONS

Hunter, E.J., et al; "Detection of Trace Nitrogen in Bulk Argon . . . ", Jour. Vac. Sci. and Tech., NY, vol. 16 No. 5, pp. 3127–3130.
EP Search Report 01110168.0 dated Feb. 14, 2003.

* cited by examiner

Primary Examiner—John R. Lee
Assistant Examiner—Zia R. Hashmi
(74) Attorney, Agent, or Firm—Geoffrey L. Chase

(57) ABSTRACT

A method for eliminating interference when analyzing a test sample of a bulk inert gas in an ion mobility spectrometer is disclosed which includes the steps of providing an ionization source for the spectrometer to form ions of the bulk inert gas, mixing a reagent gas with the test sample prior to entry into the spectrometer to alter the nature of the ions formed by the bulk inert gas to shift the location of a bulk inert gas mobility peak such that a bulk inert gas mobility peak does not overlap with an impurity mobility peak of the ions of a trace impurity of interest, whereby bulk inert gas ions are quenched and a clusters of the reagent gas and the bulk gas are formed. Alternatively, the reagent gas may be mixed with the drift gas in the ion mobility spectrometer, rather than with the test sample.

9 Claims, 2 Drawing Sheets

METHOD OF IMPROVING THE PERFORMANCE OF AN ION MOBILITY SPECTROMETER USED TO DETECT TRACE ATMOSPHERIC IMPURITIES IN GASES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to ion mobility spectrometers. More particularly, the present invention is concerned with an improved, simple and low cost method for using an ion mobility spectrometer that separates impurity ions by their mobilities.

In the past, ion mobility has been used to detect trace impurities in bulk inert gases. However, due to the low resolution of the ion mobility spectrometer, the device suffers from interference from mobility peaks generated by the bulk inert gas itself. In addition, due to the limitations of charge transfer mechanism, an ion mobility spectrometer has not been successfully used to analyze trace impurities in bulk oxygen.

Ion mobility spectrometry, as the name suggests, uses the separation of ions based on their mobilities. The separation occurs, in time, by allowing the ions to drift in a bath of gas, the drift gas, under the influence of a uniform electric field. The ions interact with the molecules of the drift gas, and this interaction is dependent on the mobility of the ions, the electric field, and the nature of the drift gas. The separation of the ions is somewhat analogous to the separation of molecules in gas chromatography, and, therefore, ion mobility spectrometry is sometimes referred to as plasma chromatography.

The prior art teaches that an ion mobility spectrometer can be used to detect trace level impurities in air. For example, U.S. Pat. No. 4,238,678 refers to the use of ion mobility spectrometer to detect the presence of very small concentrations of vapors and gases in air or other gaseous backgrounds. In an ion mobility spectrometer, the interaction time for the ions to interact with the trace impurity atoms/molecules is relatively large. This leads to the formation of cluster ions. The mobilities of the different ions produced in the interaction region, are not necessarily very different. Moreover, the resolution of a typical ion mobility spectrometer is not very large. This leads to the situation where two or more trace impurities will produce ions with similar mobility. This can prevent the unambiguous detection of the trace level impurity of interest.

It has long been recognized that water, which is omnipresent and which has a great propensity to form cluster ions, is one of the main interfering species. U.S. Pat. No. 5,457,316 refers to the use of a hermetically sealed ion mobility spectrometer for the detection of trace gases. This patent recognizes the interference problems caused by the presence of water and teaches us the need for purifying the drift gas. The '316 patent also teaches purifying the sample gas and using the purified sample gas as the drift gas. The '316 patent also teaches the use of a hermetically sealed ion mobility spectrometer so that the presence of water in the ion mobility spectrometer can be drastically reduced. The use of this invention dramatically reduces the interference problems due to water clusters. However, interfering ions generated by other co-existing trace level impurities are still present. One example of such an interfering ion is the nitrogen cluster ions $N_3^+$, $N_5^+$. In an ion mass spectrometer used to determine impurities in nitrogen, the determination of trace levels of $O_2$ will be hindered by the presence of these nitrogen cluster ions, since $O_2^+$ has the same mobility as these nitrogen cluster ions.

U.S. Pat. No. 4,551,624 refers to the use of a reagent gas to improve the specificity of an ion mass spectrometer, with the reagent gas chosen so that the electron affinity or proton affinity or acidity of the reagent gas is higher than that of the interfering species and lower than of the trace impurity of interest. This method implicitly assumes that the proton affinity, electron affinity or acidity of the interfering species is less than that of the trace impurity of interest.

U.S. Pat. No. 5,095,206 refers to the use of sulfur dioxide dopant to overcome interference problem with the detection of acid gases in air.

U.S. Pat. No. 5,283,199 provides a method for using an ion mobility spectrometer where a controlled concentration of an amine such as methylamine is added to the air carrier gas stream. The amine suppresses the chlorine peak, thereby improving the specificity of the ion mobility spectrometer to chlorine dioxide.

Finally, U.S. Pat. No. 3,621,239 generally provides methods of ion detection and separation by use of different species of reactants on a sample gas for producing predictable reactions.

It is principally desired to provide a method for improving the performance of an ion mobility spectrometer used to detect trace atmospheric impurities in gases.

It is further desired to provide a method for improving the performance of an ion mobility spectrometer used to detect trace atmospheric impurities in gases that is relatively simple and low cost.

It is further desired to provide a method for improving the performance of an ion mobility spectrometer used to detect trace atmospheric impurities in bulk inert gases where interference from mobility peaks generated by the bulk inert gas itself is minimized.

It is further desired to provide a method for improving the performance of an ion mobility spectrometer used to detect trace atmospheric impurities in bulk inert gases to analyze trace impurities in bulk oxygen.

It is still further desired to provide a method for improving the performance of an ion mobility spectrometer used to detect trace atmospheric impurities in bulk inert gases where the method provides for the separation of the mobility peaks due to interfering ions from the mobility peak due to the trace impurity of interest, so that the trace impurity of interest can be determined unambiguously.

Finally, it is desired to provide a method for improving the performance of an ion mobility spectrometer used to detect trace atmospheric impurities in bulk inert gases where a reagent gas alters the nature of the ions formed by the bulk inert gas to shift the location of a bulk inert gas mobility peak such that the bulk inert gas mobility peak does not overlap with an impurity mobility peak of the ion of a trace impurity of interest, whereby bulk inert gas ions are quenched and a cluster of the reagent gas and the bulk gas is formed.

BRIEF SUMMARY OF THE INVENTION

The present invention is directed to a method for operating an ion mobility spectrometer that uses a bulk gas and a drift gas where the spectrometer includes an analyzer cell having an ionization region, an interaction region, and a drift region, where the ionization region has an ionization source, and where the spectrometer also includes a shutter grid separating the interaction region and the drift region. The drift region has an ion current detector for detecting ions transiting the drift region and means for measuring the transit times through the drift region of ions generated in the ionization region and released into the drift region through the shutter grid. The method includes the steps of applying a drift gas stream to an inlet in the drift region, mixing a selected reagent gas with a bulk gas to create a doped bulk gas stream, applying the doped bulk gas stream to an inlet in the ionization region to carry a test sample of the doped bulk gas stream into the interaction region to form ions of the doped bulk inert gas. The process further includes measuring an ion current at the ion current detector at a time corresponding to the transit time through the drift region, of ions generated by the test sample in the interaction region. The reagent gas is selected to cause ions generated by the doped bulk gas stream in the interaction region to have transit times through the drift region different from the transit times through the drift region of ions generated by the test sample. The reagent gas is also selected for its capacity to alter the nature of the ions formed by the bulk inert gas to shift the location of a bulk inert gas mobility peak such that the bulk inert gas mobility peak does not overlap with an impurity mobility peak of the ion of a trace impurity of interest, whereby bulk inert gas ions are quenched and a cluster of the reagent gas and the bulk gas is formed.

One embodiment of the method for operating an ion mobility spectrometer includes providing the bulk inert gas as $N_2$, where the trace impurity of interest is $O_2$, and the reagent gas is Ar. Another embodiment includes providing the bulk inert gas as $O_2$, where the trace impurity of interest as $H_2O$, and the reagent gas is Ar and $H_2$.

Alternatively, rather than applying the reagent gas to the bulk gas stream, the reagent gas may be supplied as the drift gas in the ion mobility spectrometer.

DETAILED DESCRIPTION OF THE INVENTION

The present invention facilitates the separation of the mobility peaks generated by a ion mobility spectrometer due to interfering ions from the mobility peak due to the trace impurity of interest so that the trace impurity of interest can be determined unambiguously. This objective can be accomplished in two ways in accordance with the present invention. One embodiment is to add a reagent gas to the bulk inert gas which can form clusters with the interfering ions. The second embodiment is to select a drift gas that is different from the bulk inert gas being tested which can form clusters with the interfering ions.

In the first embodiment, the invention consists of adding a reagent gas to the ionization source of the ion mobility spectrometer to avoid the interference problems. The reagent gas can be chosen to tackle a specific interference problem, e.g., for the case of analyzing for trace $O_2$ in bulk $N_2$, the mobility peak of the nitrogen cluster ions overlap with the peak for the oxygen molecular ion. By the addition of up to a few percent Ar, the nitrogen cluster ions are quenched and an argon nitrogen cluster ion is formed. The mobility of this peak is different than the mobility of the molecular ion of oxygen and these two mobility peaks do not overlap.

Alternatively, in the second embodiment of the present invention, instead of using a reagent gas in the ionization region, a different drift gas can be used. Since mobilities depend upon the drift gas, the interfering mobility peaks can be separated if one uses a different drift gas.

Figure 1:
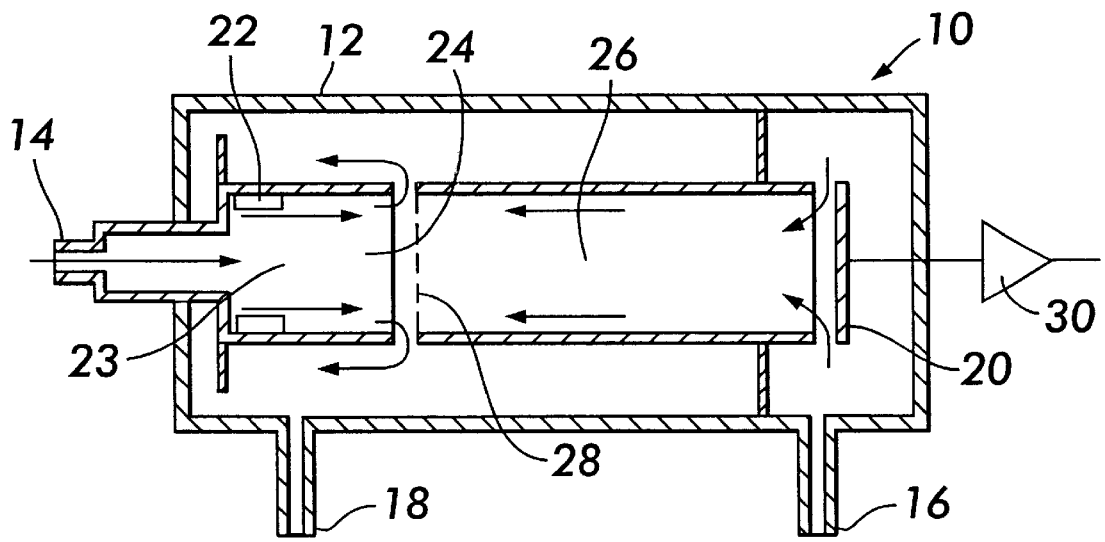
FIG. 1 is a simplified front view of an analyzer cell for an ion mobility spectrometer in accordance with one preferred embodiment of the present invention.

Referring now to the drawings, there is shown in FIG. 1, a schematic of an analyzer cell 10 for an ion mobility spectrometer for use in accordance with one preferred embodiment of the present invention. The analyzer cell 10 of the present invention preferably comprises a housing 12 having sample gas inlet port 14 to allow a sample gas to enter the cell 10, a drift gas inlet port 16 to allow the drift gas to enter the cell 10, and a vent port 18 for allowing the sample gas and drift gas to exit the analyzer cell 10. Internal to the analyzer cell 10, there is preferably a current detector, preferably in the form of collector plate 20 and an ionization source which preferably is a foil β emitter 22. The foil β emitter 22 generates ions from the sample gas.

The housing 12 is divided into an ionization region 23, an interaction region 24 and a drift region 26. The interaction region 24 and the drift region 26 are separated by a shutter or wire grid 28, as known in the art. The interaction region 24 may be, for example, about 5 cm long, while the drift region 26 may be, for example, about 7 cm long. There is a field gradient in the drift region 26 to accelerate the ions toward the collector plate 20 and then out the outlet port 16. The ionization region 23 has a β emitter 22 which preferably is a radioactive foil of $Ni^{63}$ that emits approximately 67 keV electrons and has a strength of 1 milli Curie. Additionally, it is preferable that the collector plate 20 is connected to an amplifier 30 which is used to detect a current striking the collector plate 20.

As indicated above, the electrons from the radioactive decay of the $Ni^{63}$ emitter 22 ionize the sample gas molecules. Under the influence of a uniform electric field, the ions move toward a drift region 26 in the cell 10. At atmospheric pressure, the mean free path is very small and, consequently, ion molecule reactions can rapidly occur. A counter current flow of gas, the drift gas, is maintained in the drift region 26. A purified sample gas is typically used as this drift gas.

In operation, the shutter grid 28 is periodically opened and an ion cloud is allowed to enter the drift region 26 of the spectrometer analyzer cell 10. The ion cloud moves in the drift region 26 under the influence of an electric field. The ions will be separated into different groupings, depending upon their mobilities. As each separated ion grouping arrives at the collector plate 20 at the end of the drift region 26, an electrical pulse will be detected by a detection circuit (not shown). A multichannel analyzer is typically used to average spectra from multiple openings of the electric shutter 28 to produce an ion mobility spectrum.

The mobility of an ion, $\mu$, is defined as the average velocity, $v_d$, attained by the ion under the influence of a unit electric field, while interacting with molecules present in the ambient atmosphere, or $v_d = \mu E$ or $\mu = v_d / E$ with units of cm$^2$/volt-sec.

In the weak field approximation, which is typically the case for an ion mobility spectrometer, the mobility is related to the diffusion coefficient via the Nernst-Townsend relationship, $$\mu = \frac{eD}{kT},$$

where e is the ion charge, D is the diffusion coefficient, k is the Boltzmann constant, and T is the gas temperature.

In addition to diffusion and the electric field, the motion of the ions in the drift region 26 is also affected by the electrostatic interactions between the ions and the drift gas molecules. An ion can interact with the electron cloud surrounding the drift gas molecules, thereby polarizing it and inducing a dipole moment. The ion can interact with this ion-induced dipole moment. In addition, molecules having permanent dipole or quadrupole moments will also interact with the drifting ion. It is important to realize that the mobility will depend upon not only the mass of the ion but also the charge distribution and the nature of the drift gas.

The mobility of an ion, $\mu$, depends not only on the mass of the ion and the charge distribution, but also on the interaction of the ion with the drift gas. These interactions depend upon the interaction between the ion and the ion induced dipole moment in the drift gas. Thus, the mobility will change when the drift gas is changed. Moreover, the change in mobilities will be different for different ions. By the proper choice of drift gas, it will be possible to separate the mobility peaks from the interfering ion and the ion due to the trace impurity of interest.

If the interfering ion is the result of cluster reactions in the ionization source, by adding an appropriate reagent gas, it is possible to change the nature of the cluster ion, thereby changing its mobility. This has the effect of shifting the interfering ion mobility peak so that the mobility peak due to the ion produced by the trace impurity of interest can be detected unambiguously.

As indicated above, while ion mobility spectrometry is a very sensitive detection technique, often times the mobility peak of a trace impurity is masked by a large mobility peak arising from the matrix gas. Such is the case for the detection of trace $O_2$ in $N_2$. In accordance with the first embodiment of the present invention, a trace amount of Ar is added to the interaction region 24 through the sample gas inlet port 14 (or alternatively, as in the second embodiment, Ar may be used as a drift gas added through the drift gas inlet port 16), to analyze for impurities in the $N_2$. The addition of Ar results in the formation of Ar.$N_2^+$ clusters while quenching the nitrogen ion clusters. This, in effect, shifts the mobility peaks arising from the matrix gas, $N_2$, thereby allowing the ion mobility spectrometer to sensitively detect trace $O_2$ in $N_2$.

Figure 2:
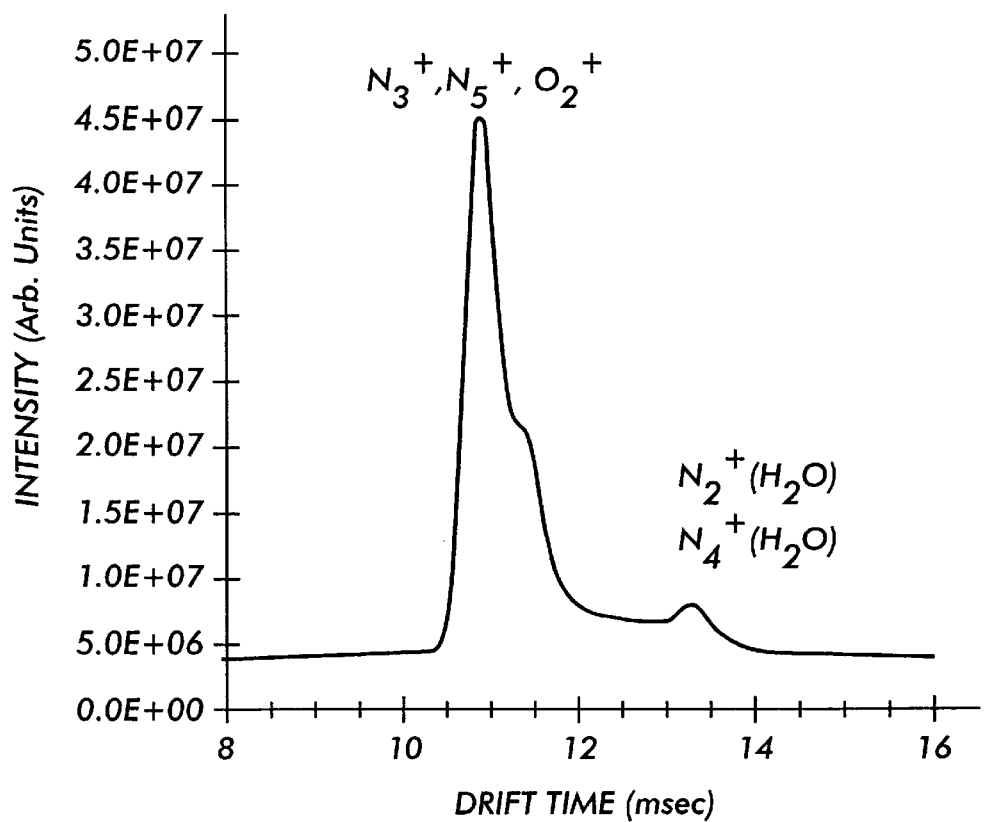
FIG. 2 is a graph of the mobility spectrum for the analysis of $N_2$ containing trace $O_2$ and $H_2O$ using purified $N_2$ as a drift gas, that does not use the process of the present invention.

If one uses an ion mobility spectrometer to detect trace $O_2$ in $N_2$ following the practice described in U.S. Pat. No. 5,457,316, it can be observed that the mobility peak produced by $O_2^+$ is coincident with the mobility peak produced by nitrogen cluster ions. These cluster ions are produced in the ionization source of the ion mobility spectrometer since $N_2$ is the sample gas. FIG. 2 shows the mobility spectrum of $N_2$ containing trace $O_2$ and $H_2O$ using purified nitrogen as a drift gas. As shown in FIG. 2, the mobility peak at 10.88 msec consists of $N_3^+$, $N_5^+$ and $O_2^+$. The major contribution to this peak is from the nitrogen cluster ions since nitrogen is the bulk constituent in the sample. Thus, it would be very difficult to detect small changes in the trace $O_2$ concentration in the sample by monitoring changes in this mobility peak.

Figure 3:
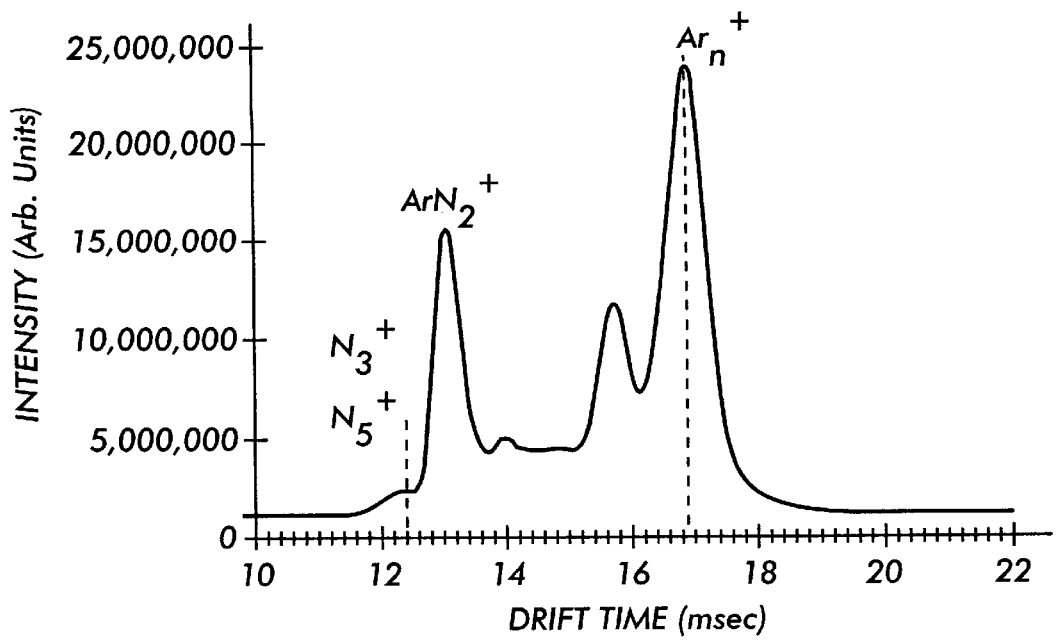
FIG. 3 is a graph of the mobility spectrum for the analysis of purified nitrogen using Ar as a drift gas obtained in accordance with the process of the present invention.

FIG. 3 shows mobility spectra for a sample of purified nitrogen using Ar as a drift gas. The different mobility peaks in this spectrum are identified in FIG. 3. The nitrogen cluster ion peak is drastically reduced with most of the ion intensity shifted to the Ar.$N_2$ cluster ion. The presence of a large cluster ion indicates that some of the drift gas is making it into the ionization region since the Ar$_n^+$ clusters can only be formed in the ionization region. A similar quenching of nitrogen cluster peaks would occur if a small amount of Ar was added into the ionization region.

Figure 4:
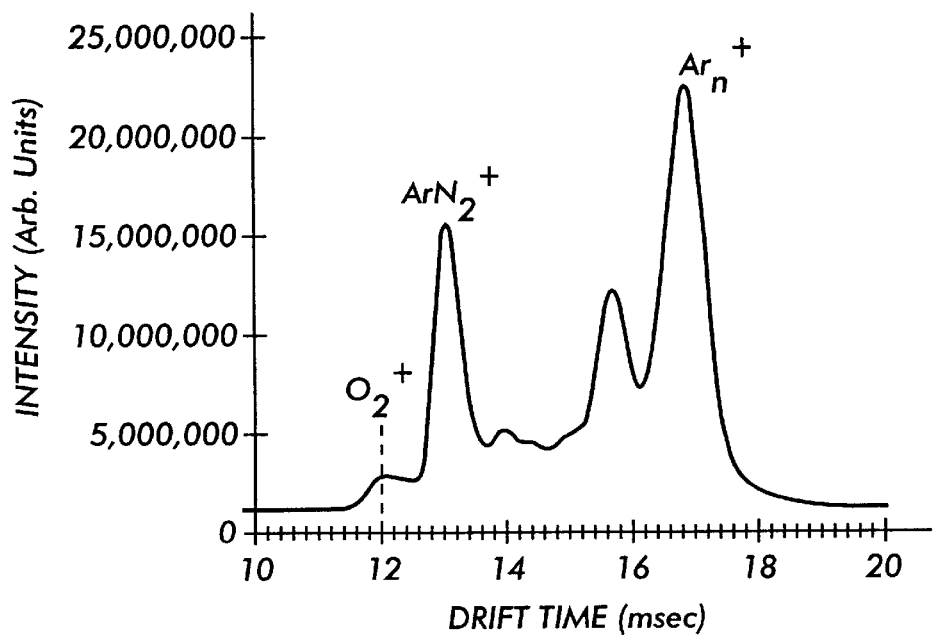
FIG. 4 is a graph of the mobility spectrum for the analysis of purified nitrogen with 0.26 parts per billion of added $O_2$ using Ar as a drift gas, in accordance with the process of the present invention.

FIG. 4 shows the spectra of a sample of purified nitrogen with 0.26 parts per billion of added $O_2$ using Ar as a drift gas. As can be seen in FIG. 4, the peak corresponding to $O_2^+$ is clearly distinguishable (in the absence of the nitrogen cluster peak). Thus, it is evident that the production of the Ar.$N_2$ cluster ion results in the unambiguous detection of trace levels of $O_2$ in $N_2$.

The above examples show the use of a reagent gas (Ar in this case) to remove the interference of unwanted cluster ions to the unambiguous detection of trace level impurities ($O_2$ in $N_2$ in this case). Similar schemes can be used for detection of trace impurities in sample gases where the ion molecule reactions are unfavorable.

In another example of the present invention, an ion mobility spectrometer can be used to detect trace $H_2O$ in $O_2$. In spite of the low ionization cross section of $O_2$, this can be accomplished since an $O_2(H_2O)^+$ cluster can easily form. However, other trace impurities cannot be detected due to the low ionization potential of $O_2$. Using the method of the present invention, this problem can be circumvented by adding Ar and $H_2$ to the sample gas inlet port 14 of the ion mobility spectrometer. The presence of $H_2$ will form ArH$^+$. This ion will undergo proton transfer reactions with the trace impurities in $O_2$, thereby aiding in their detection. Alternately, Ar and $H_2$ can be added to the source of the ion mobility spectrometer and $O_2$ can be used as a drift gas added through the drift gas inlet port 16 to accomplish the same results.

In both these examples, protonated Ar (ArH$^+$) will be generated in the ionization region. This ion has a proton affinity that is less than that of the trace level impurities and will undergo reactions to produce protonated ions of the trace impurities. These impurities can be detected at their respective mobility peaks.

In the present invention, a reagent gas is used to alter the nature of the ions formed by the bulk inert gas being analyzed. By altering the nature of the ions, the location of the mobility peak can be shifted so that it does not overlap with the mobility peak of the ion of the trace impurity of interest.

Although illustrated and described herein with reference to specific embodiments, the present invention nevertheless is not intended to be limited to the details shown. Rather, various modifications may be made in the details within the scope and range of equivalents of the claims without departing from the spirit of the invention.

What is claimed is:

1. A method for operating an ion mobility spectrometer that uses a bulk inert gas and a drift gas, said spectrometer comprising an analyzer cell having an ionization as region, an interaction region, and a drift region, said ionization region having an ionization source, said spectrometer further comprising a shutter grid separating said interaction region and said drift region, said drift region having an ion current detector for detecting ions transiting said drift region, and means for measuring transit times through said drift region of ions generated in said ionization region and released into said drift region through said shutter grid, said method comprising the steps of:

a) applying a drift gas stream to an inlet in said drift region;

b) mixing a selected reagent gas comprised of argon with a bulk inert gas to create a doped bulk inert gas stream;

c) applying said doped bulk inert gas stream to an inlet in said ionization region, to carry a test sample of said doped bulk inert gas stream into said interaction region to form ions of the doped bulk inert gas;

d) measuring an ion current at said ion current detector, at a time corresponding to a transit time through said drift region, of ions generated by said test sample in said interaction region; and e) said reagent gas comprised of argon causing ions generated by said test sample in said interaction region to have transit times through said drift region different from transit times through said drift region of ions generated by a trace impurity of interest in said test sample, said reagent gas selected for its capacity to alter the nature of the ions formed by the bulk inert gas to shift the location of a bulk inert gas mobility peak such that the bulk inert gas mobility peak does not overlap with an impurity mobility peak of the ions of the trace impurity of interest, whereby bulk inert gas ions are quenched and a cluster of the reagent comprised of argon and the bulk inert gas is formed.

2. The method for operating an ion mobility spectrometer of claim 1, wherein the bulk inert gas is $N_2$, the trace impurity of interest is $O_2$, and the reagent gas is Ar.

3. The method for operating an ion mobility spectrometer of claim 1, wherein the bulk inert gas is $O_2$, the trace impurity of interest is $H_2O$ and the reagent gas is Ar and $H_2$.

4. A method for operating an ion mobility spectrometer that uses a bulk inert gas and a drift gas, said spectrometer comprising an analyzer cell having an ionization region, an interaction region, and a drift region, said ionization region having an ionization source, said spectrometer further comprising a shutter grid separating said interaction region and said drift region, said drift region having an ion current detector for detecting ions transiting said drift region, and means for measuring transit times through said drift region of ions generated in said ionization region and released into said drift region through said shutter grid, said method comprising the steps of:

a) selecting a reagent comprised of argon as a drift gas, said reagent selected to cause ions generated by a bulk inert gas stream in said interaction region to have transit times through said drift region different from transit times through said drift region of ions generated by a trace impurity of interest, said reagent gas selected for its capacity to alter the nature of the ions formed by the bulk inert gas to shift the location of a bulk inert gas mobility peak such that the bulk inert gas mobility peak does not overlap with an impurity mobility peak of the ions of trace impurity of interest;

b) applying said bulk inert gas stream to an inlet in said ionization region, to carry a test sample of said bulk inert gas stream into said interaction region; and c) applying said drift gas in a stream to an inlet in said drift region; and d) measuring an ion current at said ion current detector, at a time corresponding to a transit time through said drift region, of ions generated by said test sample in said interaction region, whereby bulk inert gas ions are quenched and a cluster of the reagent gas and the bulk inert gas is formed.

5. The method for operating an ion mobility spectrometer of claim 4, wherein the bulk inert gas is $N_2$, the trace impurity of interest is $O_2$, and the reagent gas is Ar.

6. The method for operating an ion mobility spectrometer of claim 5, wherein the bulk inert gas is $O_2$, the trace impurity of interest is $H_2O$ and the reagent gas is Ar and $H_2$.

7. A method for eliminating interference when analyzing a test sample of a bulk inert gas in an ion mobility spectrometer, the method comprising the steps of:

providing an ionization source for the ion mobility spectrometer to form ions of the bulk inert gas;

mixing a reagent gas comprised of argon with the test sample prior to entry into said ion mobility spectrometer, to alter the nature of the ions formed by the bulk inert gas to shift the location of a bulk inert gas mobility peak such that the bulk inert gas mobility peak does not overlap with an impurity mobility peak of ions of a trace impurity of interest, whereby bulk inert gas ions are quenched and a clusters of the reagent gas and the bulk inert gas are formed.

8. The method for eliminating interference of claim 7 wherein the bulk inert gas is $N_2$, the trace impurity of interest is $O_2$, and said spectrometer uses Ar as a drift gas.

9. The method for eliminating interference of claim 7, wherein the bulk inert gas is $O_2$, the trace impurity of interest is $H_2O$ and said spectrometer uses a Ar and $H_2$ as a drift gas.

* * * * *